United States Patent [19]

Kotliar et al.

[11] Patent Number: 4,891,263

[45] Date of Patent: Jan. 2, 1990

[54] POLYCARBONATE RANDOM COPOLYMER-BASED FIBER COMPOSITIONS AND METHOD OF MELT-SPINNING SAME AND DEVICE

[75] Inventors: Abraham M. Kotliar, Westfield; William J. Boyle, Jr., Denville; Reginald T. Tang, Warren; Frank Mares, Whippany; Kundanbhai M. Patel, Landing; Tin-Ho Chiu, Millburn, all of N.J.

[73] Assignee: Allied-Signal Inc., Morris Township, Morris County, N.J.

[21] Appl. No.: 134,321

[22] Filed: Dec. 17, 1987

[51] Int. Cl.$^4$ .................. C08G 63/64; C08G 63/62
[52] U.S. Cl. ........................... 428/225; 528/86; 528/271; 528/354; 528/370; 604/890.1; 606/230
[58] Field of Search ............... 528/354, 370, 271, 86; 428/225

[56] References Cited

U.S. PATENT DOCUMENTS

| | | | |
|---|---|---|---|
| 3,248,414 | 4/1966 | Stevens | 528/196 X |
| 3,301,824 | 1/1967 | Hostettler et al. | 528/370 X |
| 3,301,825 | 1/1967 | Hostettler et al. | 528/370 X |
| 3,305,605 | 2/1967 | Hostettler et al. | 528/370 X |
| 3,324,070 | 6/1967 | Hostettler et al. | 528/357 X |
| 3,379,693 | 4/1968 | Hostettler et al. | 528/370 X |
| 3,758,443 | 9/1973 | Konig et al. | 260/75 NP |
| 3,952,016 | 4/1976 | Barillo et al. | 260/340.2 |
| 3,959,185 | 5/1976 | Barillo et al. | 252/522 |
| 4,052,988 | 10/1977 | Doddi et al. | 128/335.5 |
| 4,070,375 | 1/1978 | Suzuki | 260/340.6 |
| 4,079,038 | 3/1978 | Choi et al. | 260/47 X |
| 4,157,437 | 1/1979 | Okuzummi et al. | 528/354 |
| 4,160,853 | 7/1979 | Ammons et al. | 428/425 |
| 4,190,720 | 2/1980 | Shalaby | 528/354 |
| 4,243,775 | 1/1981 | Rosensaft et al. | 525/415 |
| 4,300,565 | 11/1981 | Rosensaft et al. | 128/335.5 |
| 4,423,205 | 12/1983 | Rajan | 528/371 |
| 4,429,080 | 1/1984 | Casey et al. | 528/354 X |
| 4,562,022 | 12/1985 | Li et al. | 264/54 |
| 4,705,820 | 11/1987 | Wang et al. | 528/354 X |
| 4,791,929 | 12/1988 | Jarrett et al. | |

FOREIGN PATENT DOCUMENTS 1272733 5/1972 United Kingdom.

*Primary Examiner*—Earl Nielsen
*Attorney, Agent, or Firm*—Richard C. Stewart; Gerhard H. Fuchs

[57] ABSTRACT

This invention is directed to novel random copolymers and implantable devices fabricated therefrom.

43 Claims, No Drawings

POLYCARBONATE RANDOM COPOLYMER-BASED FIBER COMPOSITIONS AND METHOD OF MELT-SPINNING SAME AND DEVICE

FIELD OF THE INVENTION

This invention relates to bioresorbable random copolymers comprising at least one carbonate unit as the major component, said carbonate copolymerized with at least one second monomeric component. It also related to fibers and other devices formed from said random copolymers. These copolymers are especially suited for use in devices for implantation into living tissue.

BACKGROUND OF THE INVENTION

Polycarbonates have been known for a number of years. U.S. Pat. No. 3,301,824 (1967) describes the preparation of carbonate homopolymers and random copolymers with cyclic lactones. While the patent generally discloses that the polymers have utility in moldings, coatings, fibers and plasticizers, there is no appreciation whatsoever of biodegradable fibers composed in whole or in part of polycarbonate "biopolymers".

In addition, there is no appreciation for the usefulness and importance of substituted poly(aliphatic carbonates) as fiber-forming polymeric compositions. By contrast, it is caprolactone, the dominant co-monomer, which offers the necessary crystalline character needed for fiber formation.

U.S. Pat. Nos. 4,243,775 (1981) and 4,429,080 (1984) disclose the use of polycarbonate-containing polymers in certain medical applications, especially sutures and other medical fasteners. However, this disclosure is clearly limited only to "ABA" and "AB" type block copolymers where only the "B" block contains poly(trimethylene carbonate) or a random copolymer of glycolide with trimethylene carbonate. The A block is necessarily limited to polyglycolide, which confers the crystalline character in the polymer necessary for fiber formation; and thus, the major portion of the polymers is the glycolide.

Accordingly, the art has failed to fully appreciate the potential biological or medical uses of biopolymers based on carbonates, especially with respect to their biodegradable or bioresorbable properties, as well as the wide range of mechanical properties achievable with these materials.

Bioresorbable polymers have been used in the fabrication of devices for implantation in living tissue for several decades. Medical application of such polymers include absorbable sutures, haemostatic aids and, recently, intraosseous implants and slow-release drug delivery systems, to name but a few.

Use of such polymers has been extended to tissue regeneration devices such as nerve channels, vascular grafts, sperm duct channels, fallopian tube ducts or channels and the like. To be effective, these devices must be made from materials that meet a wide range of biological, physical, and chemical prerequisites. The material must be bioresorbable at least in part, nontoxic, noncarcinogenic, nonantigenic, and must demonstrate favorable mechanical properties such as flexibility, suturability in some cases, and amenability to custom fabrication. The biopolymers of the present invention have all of those attributes.

SUMMARY OF THE INVENTION

The present invention provides copolymers comprising as a minor component, i.e., less than about 50 weight % based on the total weight of all recurring monomeric units, at least one recurring monomeric unit, and as a major component, i.e., more than about 50 weight % based on the total weight of all recurring carbonate monomeric units, a carbonate monomeric unit chosen from carbonate units of the following General Structures I and II:

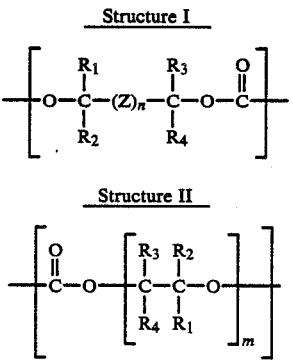

wherein

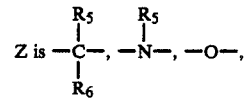

combination thereof, where Z is selected such that there are no adjacent heteroatoms;

n and ma re the same or different and are integers from about 1 to 8;

$R_1$, $R_2$, $R_3$, and $R_4$ are the same or different at each occurrence and are hydrogen, alkoxyaryl, aryloxyaryl, arylalkyl, alkylarylalkyl, arylalkylaryl, alkylaryl, arylcarbonylalkyl, aryloxyalkyl, alkyl, aryl, alkylcarbonylalkyl, cycloalkyl, arylcarbonylaryl, alkylcarbonylaryl, alkoxyalkyl, or phenyl or alkyl substituted with one or more biologically compatible substituents such as alkyl, aryl, alkoxy, aryloxy, dialkylamino, diarylamino, alkylarylamino substituents;

$R_5$ and $R_6$ are the same or different and are $R_1$, $R_2$, $R_3$ $R_4$, dialkylamino, diarylamino, alkylarylamino, alkoxy, aryloxy, alkanoyl, or arylcarbonyl; or any two of $R_1$ to $R_6$ together can form an alkylene chain completing a 3, 4, 5, 6, 7, 8 or 9 membered monocyclic fused, alicyclic, spiro, bicyclic and/or tricyclic ring system, which system may optionally include one or more nonadjacent carbonyl, oxa, alkylaza or arylaza groups;

and provided that at least one of $R_1$ to $R_6$ is other than hydrogen.

Another aspect of this invention relates to implantable medical devices and fibers formed from the novel copolymers of this invention, and to prosthetic devices, i.e., sutures, vascular grafts, nerve growth channels, tendon and ligament replacements, and the like, fabricated totally or in part from said fibers.

The present invention is based on the discovery that certain aliphatic carbonates can form highly crystalline random copolymers with other monomer components, as long as the appropriate carbonate is present as the major component. The novel copolymers provided by this invention have relatively high modulus and tensile strength, and can be readily processed to fibers of various deniers, depending on the applications desired. These copolymers also exhibit controllable biodegradation rates, blood compatability, and biocompatibility with living tissue. These copolymers also induce minimal inflammatory tissue reaction, as biodegradation of the carbonate polymer by hydrolytic depolymerization results in degradation substances having physiologically neutral pH. These particular qualities render fibers made from the copolymers suitable for medical applications such as vascular grafts, wound and skin covers, sutures, hemostatic aids, materials for tendon or ligament repair, bone or dental repair, and the like.

DETAILED DESCRIPTION OF THE INVENTION

The bioresorbable copolymers of the invention are random copolymers comprising as a minor component one or more recurring monomeric units, and as a major component, a recurring carbonate monomeric unit of General Structures I and II:

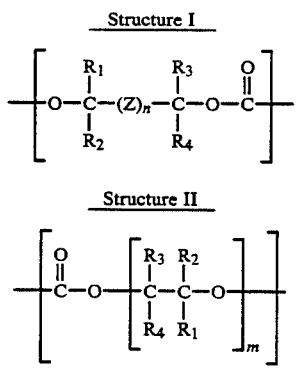

wherein

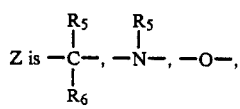

combination thereof, where Z is selected such that there are no adjacent heteroatoms:

n and m are the same or different and are integers from about 1 to 8; and $R_1$, $R_2$, $R_3$, and $R_4$ are the same or different at each occurrence and are hydrogen, alkoxyaryl, aryloxyaryl, arylalkyl, alkylarylalkyl, arylalkylaryl, alkylaryl, arylcarbonylalkyl, aryloxyalkyl, alkyl, aryl, alkylcarbonylalkyl, cycloalkyl, arylcarbonylaryl, alkylcarbonylaryl, alkoxyalkyl, or phenyl or alkyl substituted with one or more biologically compatible substituents such as alkyl, aryl, alkoxy, aryloxy, dialkylamino, diarylamino, alkylarylamino substituents;

$R_5$ and $R_6$ are the same or different and are $R_1$, $R_2$, $R_3$ $R_4$, dialkylamino, diarylamino, alkylarylamino, alkoxy, aryloxy, alkanoyl, or arylcarbonyl; any two of $R_1$ to $R_6$ together can form an alkylene chain completing a 3, 4, 5, 6, 7, 8 or 9 membered monocyclic, alicyclic, spiro, bicyclic and/or tricyclic ring system, which system may optionally include one or more non-adjacent carbonyl, oxa, alkylaza or arylaza groups;

with the proviso that at least one of $R_1$ to $R_6$ is other than hydrogen.

Illustrative of useful $R_1$, $R_2$, $R_3$, and $R_4$ groups are hydrogen; alkyl such as methyl, ethyl, propyl, butyl, pentyl, octyl, nonyl, tert-butyl, neopentyl, isopropyl, sec-butyl, dodecyl and the like; cycloalkyl such a cyclohexyl, cyclopentyl, cyclooctyl, cycloheptyl and the like; alkoxyalkyl such as methoxymethylene, ethoxymethylene, butoxymethylene, propoxyethylene, pentoxybutylene and the like; aryloxyalkyl and aryloxyaryl such as phenoxyphenylene, phenoxymethylene and the like; and various substituted alkyl and aryl groups such as 4-dimethylaminobutyl, and the like;

Illustrative of other $R_1$ to $R_4$ groups are divalent aliphatic chains, which may optionally include one or more oxygen, trisubstituted amino or carbonyl group, such as —(CH$_2$)$_2$—, —CH$_2$(O)CH$_2$—, —(CH$_2$)$_3$—, —CH$_2$—CH(CH$_3$)—, —(CH$_2$)$_4$—, —(CH$_2$)$_5$—, —CH$_2$OCH$_2$—, —(CH$_2$)$_2$—N(CH$_3$)CH$_2$—, —CH$_2$C(O)CH$_2$—, —(CH$_2$)$_2$—N(CH$_3$)—(CH$_2$)$_2$—, and the like and divalent chains to form fused, spiro, bicyclic or tricyclic ring systems, such as —CH(CH$_2$CH$_2$)$_2$CH—, —CH(CH$_2$CH$_2$CH$_2$)$_2$CH—, —CH(CH$_2$)(CH$_2$CH$_2$)CH—, —CH(CH$_2$)(CH$_2$—CH$_2$CH$_2$)CH—, —CH(C(CH$_3$)$_2$)(CH$_2$CH$_2$)CH—, and the like.

Illustrative of useful $R_5$ and $R_6$ groups are the above-listed representative $R_1$ to $R_4$ groups, including "OCH$_2$C(O)CH$_2$", "(CH$_2$)$_2$—NCH$_3$—", —OCH$_2$C(O)CH$_2$—, —O—(CH$_2$)$_2$—O—, alkoxy such as propoxy, butoxy, methoxy, isopropoxy, pentoxy, nonyloxy, ethoxy, octyloxy, and the like; dialkylamino such as dimethylamino, methylethylamino, diethylamino, dibutylamino, and the like; alkanoyl such as propanoyl, acetyl, hexanoyl, and the like, arylcarbonyl such as phenylcarbonyl, p-methylphenyl carbonyl, and the like; and diarylamino and arylalkylamino such as diphenylamino, methylphenylamino, ethylphenylamino and the like.

Preferred for use in the practice of this invention are random copolymers comprising as a major component, carbonate recurring units of General Structure I wherein:

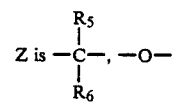

or a combination thereof; n is 1, 2 or 3; and $R_1$ to $R_6$ are as defined above, preferably where aliphatic moieties included in $R_1$ to $R_6$ include up to about 10 carbon atoms and the aryl moieties include up to about 16 carbon atoms.

Illustrative of these preferred copolymers are those wherein in the major component n is 1 and Z is of the formulas:

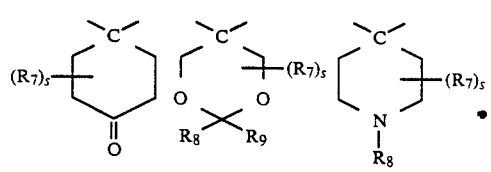

-continued

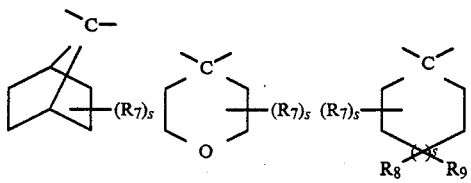

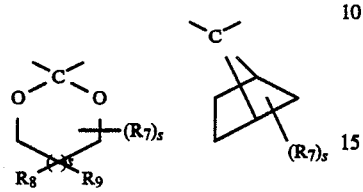

Where —C— denotes the center carbon atom of Z, when Z is —C(R$_5$)(R$_6$)—; R$_7$ is the same or different and are aryl, alkyl or an alkylene chain completing a 3 to 16 membered ring structure, including fused, spiro, bicyclic and/or tricyclic structures, and the like; R$_8$ and R$_9$ are the same or different at each occurrence and are R$_7$ or hydrogen, and s is the same or different at each occurrence and is 0 to about 3, and the open valencies are substituted with hydrogen atoms.

Also illustrative of these preferred major components are those comprising recurring units of the formula:

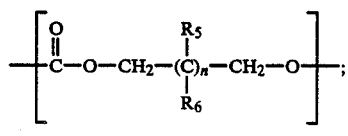

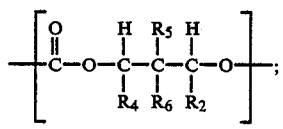

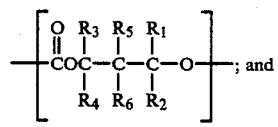

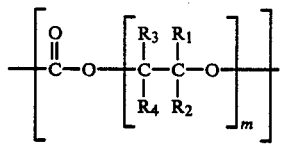

wherein:

R$_1$, R$_2$, R$_3$, and R$_4$, are the same or different at each occurrence and are hydrogen, alkyl such as methyl, ethyl, n-propyl, isopropyl, n-butyl, sec-butyl, t-butyl, neopentyl, and the like; phenyl; anisyl; phenylalkyl, such as benzyl, phenethyl, and the like; phenyl substituted with one or more alkyl or alkoxy groups such as tolyl, xylyl, p-methoxyphenyl, m-ethoxyphenyl, p-propoxyphenyl, and the like; and alkoxyalkyl such as methoxymethyl, ethoxymethyl and the like; R$_5$ and R$_6$ are the same or different and are R$_1$ to R$_4$, alkoxy, alkanoyl, arylcarbonyl, dialkylamino; or any two of R$_1$ to R$_6$ together may form alkylene chain completing 4, 5, 6, 7, 8 or 9 membered monocyclic, spiro, bicyclic and/or tricyclic ring structure which structure may optionally include one or more non-adjacent divalent carbonyl, oxa, alkylaza or arylaza groups with the proviso that at least one of R$_1$ or R$_6$ is other than hydrogen; and n and m are the same or different and are 1, 2 or 3.

Particularly preferred for use in the practice of this invention are random copolymers comprising as a major component, recurring units of the formula:

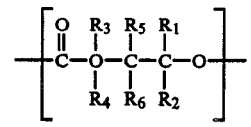

wherein:

R$_1$ to R$_4$ are the same or different and are alkyl, hydrogen, alkoxyalkyl, phenylalkyl, alkoxyphenyl, or alkylphenyl, wherein the aliphatic moieties include from 1 to about 9 carbon atoms; and R$_5$ and R$_6$ are the same or different at each occurrence and are selected from the group consisting of R$_1$ to R$_4$ substituents, aryloxy, and alkoxy, or R$_5$ and R$_6$ together may form an aliphatic chain completing a 3 to 10 membered spiro, bicyclic, and/or tricyclic structure which may include one or two non-adjacent oxa, alkylaza or arylaza groups, with the proviso that at least one of R$_1$ to R$_6$ is other than hydrogen.

In the most preferred embodiments of this invention, the random copolymer comprises as a major component, recurring monomeric units of Structure III;

Structure III

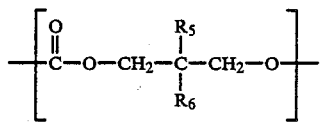

wherein:

R$_5$ and R$_6$ are the same or different and are hydrogen, phenyl, phenylalkyl, or phenyl or phenylalkyl substituted with one or more alkyl or alkoxy groups; or alkyl or R$_5$ and R$_6$ together make a divalent chain forming a 3 to 10 membered spiro, bicyclic, and/or tricyclic ring structure which may include one or two non-adjacent carbonyl, oxa, alkylaza or arylaza groups, with the proviso that at least one of R$_5$ and R$_6$ is other than hydrogen.

It is more preferred that the random copolymer comprises as a major component, recurring monomeric units of Structure III, particularly when R$_5$ and R$_6$ are the same or different and are alkyl, phenyl, phenylalkyl, or phenyl or phenylalkyl substituted with one or more alkyl or alkoxy groups; or a divalent chain forming a 3 to 10 membered, preferably 5 to 7, spiro or bicyclic ring structure which may optionally include one or two non-adjacent oxa, carbonyl, or, disubstituted amino groups. It is particularly preferred that R$_5$ and R$_6$ are the same or different and are phenyl, alkylphenyl or phenylalkyl such as, tolyl, beneyl, phenethyl or phenyl, or lower alkyl of from 1 to about 7 carbon atoms such as methyl, ethyl, propyl, isopropyl, n-butyl, tertiary butyl, pentyl, neopentyl, hexyl, and secondary butyl.

In the most preferred embodiments utilizing Structure III, R$_5$ and R$_6$ are the same or different, and are lower alkyl having from about 1 to about 4 carbon atoms, and do not differ from each other by more than about 3 carbon atoms, and preferably by not more than about 2 carbon atoms. It is particularly preferred that $R_5$ and $R_6$ be the same and be alkyl of about 1 to 2 carbon atoms, and most preferably methyl for each of $R_5$ and $R_6$.

As a necessary minor component, the copolymers include one or more other recurring monomer units. The minor component of the random copolymers of the invention may vary widely. The only requirement is that the component is sufficient to modify the degree of crystallinity in the copolymer so that the copolymer can be spun into a fiber having the desired mechanical and physiological characteristics. It is preferred that the minor component is also bioresorbable.

Illustrative of the second recurring monomeric components are those derived from carbonates, including but not limited to, certain of the monomeric units included within the scope of General Structure I with $(Z)_n$ being from 0 to 8 for n and General Structures II and III, particularly those less preferred as the major component, and those derived from substituted or non-substituted ethylene carbonates, tetramethylene carbonates, trimethylene carbonates, pentamethylene carbonates, and the like. Also illustrative of the second recurring monomeric unit are those which are derived from monomers which polymerize by ring opening polymerization as, for example, substituted and unsubstituted beta, gamma, delta, omega, and other lactones such as those of the formula:

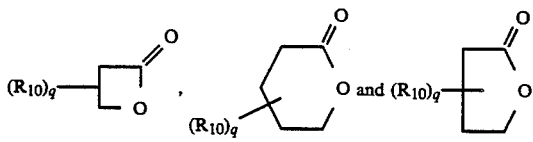

where $R_{10}$ is alkoxy, alkyl or aryl, and q is 0 to about 3, wherein the open valencies are substituted with hydrogen atoms. Such lactones include caprolactones, valerolactones, butyrolactones, propiolactones, and the lactones of hydroxy carboxylic acids such as 3-hydroxy-2-phenylpropanoic acid, 3-hydroxy-3-phenylpropanoic acid, 3-hydroxybutanoic acid, 3-hydroxybutanoic acid, 3-hydroxy-3-methylbutanoic acid, 3-hydroxypentanoic acid, 5-hydroxypentanoic acid, 3-hydroxy-4-methylheptanoic acid, 4-hydroxyoctanoic acid, and the like; and lactides such as l-lactide, d-lactide, and d,l-lactide; glycolide; and dilactones such as those of the formula:

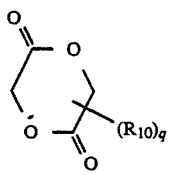

where $R_{10}$ and q are as defined above and where the open valencies are substituted with hydrogen atoms. Such dilactones include the dilactones of 2-hydroxycarboxylic acids such as 2-hydroxybutyric acid, 2-hydroxy-2-phenylpropanoic acid, 2-hydroxyl-3-methylbutanoic acid, 2-hydroxypentanoic acid, 2-hydroxy-4-methylpentanoic acid, 2-hydroxyhexanoic acid, 2-hydroxyoctanoic acid, and the like.

Illustrative of still other useful minor components are units derived from idoxepanones such as those described in U.S. Pat. No. 4,052,988 and U.K. Patent No. 1,273,733. Such dioxepanones include alkyl and aryl substituted and unsubstituted dioxepanones of the formula:

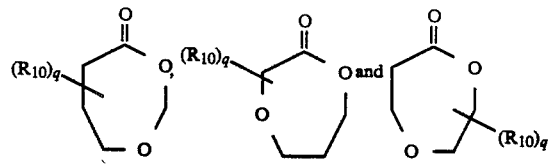

and monomeric units derived from dioxanones such as those described in U.S. Pat. Nos. 3,952,016, 4,052,988, 4,070375, and 3,959,185, as for example, alkyl or aryl substituted and unsubstituted dioxanones of the formula:

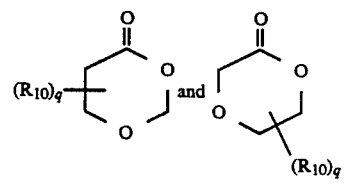

wherein q is as defined above; $R_{10}$ is the same or different at each occurrence and are hydrocarbyl groups such as alkyl and substituted alkyl, and aryl or substituted aryl; and the open valencies are substituted with hydrogen atoms. Preferably $R_{10}$ is the same or different and are alkyl groups containing from 1 to 6 carbon atoms, preferably 1 or 2 carbon atoms, and q is 0 or 1.

Suitable minor components also include monomeric units derived from ethers such as 2,4-dimethyl-1,3dioxane, 1,3-dioxane, 1-,4-dioxane, 2-methyl-5-methoxy-1, 3-dioxane, 4-methyl-1,3-dioxane, 4-methyl-4-phenyl-1, 3-dioxane, oxetane, tetrahydrofuran, tetrahydropyran, hexamethylene oxide, heptamethylene oxide, octamethylene oxide, nonamethylene oxide, and the like.

Still other useful minor components include monomeric units derived from epoxides such as ethylene oxide, propylene oxide, alkyl substituted ethylene oxides such as ethyl, propyl, and butyl substituted ethylene oxide, the oxides of various internal olefins such as the oxides of 2-butene, 2-pentene, 2-hexene, 3-hexene, and like epoxides; and also including units derived from epoxides with carbon dioxide; and monomeric units derived from orthoesters or orthocarbonates such as alkyl or aryl substituted or unsubstituted orthoesters, orthocarbonates, and cyclic anhydrides which may optionally include one or more oxa, alkylaza, arylaza, and carbonyl groups of the formula:

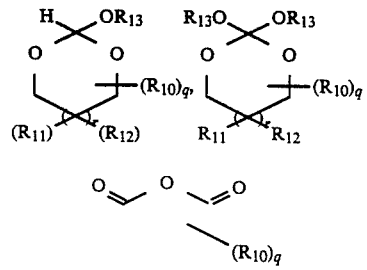

where q and $R_{10}$ are as described above, r is 0 to about 10, $R_{13}$ is the same or different at each occurrence and is alkyl or aryl, and $R_{11}$ and $R_{12}$ are the same or different and are hydrogen, alkyl or aryl.

Monomeric units derived from precursors and derivatives of lactides, lactones, dioxanones, orthoesters, orthocarbonates, anhydrides, and dioxepanones such as the various hydroxycarboxylic acids, substituted or non-substituted diacids such as oxa, aza, alkyl, aryl, substituted diacids, hydroxy substituted oxacarboxylic acids, functionalized esters, and acid halide derivatives, and the like can also be used as the minor component.

Preferred minor components are recurring monomeric units within the scope of Structures I and II and those derived from lactones, lactides and their precursors; orthoesters; dioxepanones; dioxanones; and orthocarbonates; which are bioresorbable. Particularly preferred for use as the minor component are those derived from gamma, delta, and omega lactones and their precursor acids such as caprolactone, valerolactone, butyrolactone and 3-hydroxybutanoic acid, 4-hydroxybutanoic acid, propiolactone; lactides and their precursor acids such as l-lactide, d-lactide, d,1-lactide; 2-hydroxyisobutyric acid, 2-hydroxy-2-phenylpropanoic acid, and the like; dioxepanones; dioxanones; carbonates such as trimethylene carbonates, tetramethylene carbonates, dimethylene carbonates and the like; and orthoesters and orthocarbonates. Most preferred for use in the practice of this invention as the minor component are recurring monomeric units derived from lactones, carbonates and lactides and their precursors, with units derived from lactones (especially valerolactone and caprolactone); carbonates (especially trimethylene carbonate); and lactides (especially d,1-lactide) being the units of choice.

Relative percentages of each of the recurring monomeric units that make up the copolymers of the invention vary widely. The only requirement is that at least one type of recurring monomeric unit within the scope of General Structure I be in the major amount, and that other type or recurring unit or units be in the minor amount. The minor component is preferably in an amount which does not prevent crystallization of the resulting copolymers, however, which is sufficient to improve spinnability and drawability of the fiber. As used herein, "major amount" is more than about 50 weight % based on the total weight of all recurring monomeric units in the copolymer and "minor amount" is less than about 50 weight % based on the total weight of all recurring monomeric units in the copolymer.

In the preferred embodiments of the invention, then, the amount of the minor recurring unit is an amount that is effective to provide a copolymer having a degree of crystallinity which will modify the crystallinity of the copolymer such that it then will become more suitable for fiber formation.

In addition, for certain applications, end-capping of these biopolymers may be desirable. End-capping by, e.g., acylating, alkylating, silylating agents and the like are definitely within the scope of this invention. Also included are chain extending, and various grafting or other units, monomeric, oligomeric or polymeric, or otherwise. These are techniques well known in the art of polymer science.

Thus, one of skill in the art will appreciate that the relative ranges may be adjusted according to the major and minor components of choice and the desired crystallinity of the claimed copolymer. When the copolymer will be spun into a fiber, relative ranges may be adjusted according to the spinning technique utilized and reaction parameters employed, as well as the intended use of the fiber and its desired attributes. For example, using preferred major components and preferred minor components, weight % of the major component may range from about 51% to slightly less than 100% based on the total weight of recurring units in the copolymer, preferably from about 80% to about 99%, and most preferably from about 90% to about 98%.

The copolymers of this invention are useful in the fabrication of totally or partially bioresorbable medical devices. These devices take many forms depending on intended use. Illustrative of useful devices which may be fabricated from the copolymers of this invention are orthopedic devices such as pins, plates, clamps, screws and plates; vascular implants or supports such as arterial grafts; clips; staples; nerve channels or supports; and the like. Illustrative of still other devices which can be fabricated totally or in part from the copolymers of this invention are devices for tendon and ligament replacement, breast prostheses, dental packs, sponges, hernia patches, burn dressings, absorbant swabs, and the like. Devices fabricated from the copolymers of this invention may be totally bioresorbable or may be fabricated in part from biodurable materials which are relatively resistant to biodegradation. Illustrative of useful biodurable materials are silicone, silicone rubber, polyethylene, polyethylene terephthalate, polyfluoroethylene, polyphosphazene, polyurethane, segmented polyurethane, and the like. Also useful are biodurable metallic substances such as titanium, stainless steel, and alloys such as chrominium-cobalt-molybelenum alloys, titanium-aluminum-vanadium alloys, and the like.

The copolymers of the invention are particularly suited to be spun into fibers by any suitable fiber-forming technique, which fibers can then be fabricated in useful medical devices using conventional techniques. For example, fibers made from the polymers of the present invention may be formed by conventional processes such as spinning techniques, including melt, solution, dry, gel and the like. Methods for spinning fibers from copolymers and polymers are well known in the art and will not be described herein in great detail. For example, such techniques are described in Fundamentals of Fiber Formations by Androzej Zibuke, Wiley and Sons, 1976 (New York), and like publications.

The molecular weight of the copolymer may vary widely depending on the use. In general, the molecular weight of the copolymer is sufficiently high to allow its use in the fabrication of medical devices. In the preferred embodiments of this invention where the copolymers are used in the formation of fibers, the copolymers are of "fiber-forming molecular weight." As used herein, a "fiber-forming molecular weight" is a molecular weight which is such that the copolymer can be spun into a fiber. Such molecular weights and their selections are well known in the art.

Useful average molecular weight ranges of the copolymers for use in any particular situation will vary widely depending on the ultimate fiber properties and characteristics it is desired to obtain, such as modulus, tensile strength, bioresorption and biodegradation rates, and the like. In general, copolymer molecular weights useful for forming fibers of the invention are equal to or greater than about 10,000. Preferred average molecular weight ranges are from about 10,000 to about 5,000,000, with a range of from about 20,000 to about 1,000,000 being particularly preferred, and a range of from about 30,000 to about 500,000 being most preferred.

Other polymeric components such as fillers and binders may be combined with the copolymers prior to and during the formation of fibers or devices, or subsequent to their formation. These includes, but are not limited to polymers and copolymers selected from the group consisting of polyesters such as poly(butylene-terephthalate) and poly(ethyleneterephthalate); polyvinylalcohol; polyvinylacetate and partially hydrolyzed forms thereof; hydrogel type polymers such as poly hydroxyethylmethacrylate, poly hydroxypropylmethacrylate, and the like; polysulfones such as polyphenylenesulfone; carbon; silicon carbide; halopolymers such as poly(tetrafluoroethylene) ethylene/tetrafluoroethylene copolymer; polydioxanone; polyglycolideco-trimethylene carbonates; polylactides; poly-d-lactide; polylactide-co-caprolactone; poly-d,1-lactide; polycaprolactones; polyhydroxybutyrates; poly hydroxyvalerates; polyhydroxybutyrate-co-hydroxyvalerates; polyglycolide; polyurethanes; segmented polyurethanes; polyetherurethanes; polyurethane ureas; silicone rubber; and substances such as fibrin and its powder; natural or processed collagen; mono-saccharides, di-saccharides, tri-saccharides, and polysaccharides; polyethylenes; polyamides; polypropylene, polycarbonates; poly(vinyl fluordie); poly(vinylidene fluoride); poly(vinyl butyral); cellulose such as, carboxylmethyl cellulose, cellulose acetate, ethylcellulose, and the like; ethylene-vinylacetate copolymers and hydrolyzed and partially hydrolyzed forms thereof; polyacrylonitrile; poly(vinylmethylether); and their derivatives, copolymers and the like.

It is also within the contemplation of the invention that fibers be formed by co-extrusion of different components, organic or inorganic in nature and polymeric or otherwise, together with the polycarbonate fiber materials of the invention. These include, but are not limited to, sheath-core and multiple component, multi-layered types of fiber as well as hollow fibers and especially hollow fibers or tubings of concentric multiple layered configurations.

Other components besides polymeric components may be combined with the polymers during or before they are formed into the fibers of the invention, or added to, coated onto and the like, after their formation. These components include substances that will enhance certain of the desired properties of fibers made from the polymers. Among the contemplated classes of such substances are plasticizers, lubricants, antioxidants, stabilizers of all kinds such as stabilizers for UV, heat, moisture, and the like, as well as drugs for treatment of certain disorders or diseases. Materials such as calcium phosphate salts, ceramics, bioresorbable or otherwise, such as calcium hydroxyapatite, Bioglass, and calcium triphosphate are included. Components such as certain barium salts to render the fibers and devices formed from the radio-opaque are also within the contemplation of the invention. Certain of these fillers, binders, additives and components can be removed or leached from such fibers, at some stage, so that a porous or semi-porous system can be obtained. In addition, gas foaming during the extrusion of the fibers either by gaseous, e.g., $N_2$, He, Ar, Ne, Air, and the like, and/or their combinations, or chemical foaming agents, can be utilized to achieve a porous or somewhat porous fiber structure.

Shapes of the fibers can vary. Shapes such as round, oval, square, rectangular, star shaped, shaped generally characterized as multilobal such as trilobal and hexalobal, semispherical, semitorroidal, semiarched, -bowed, -oblong, and their combinations and the like are included. Cross-sectional dimensions as well as surface properties such as roughness, smoothness, striations on the long axis as well as circumferential ridges and valleys and the like are important with respect to intended use. Hollow fibers are also included. For example, smooth fibers may be important for applications such as vascular graft, woven or knitted from such smooth fibers; striated fibers may be important as ligament or tendon prosthesis to encourage certain alignment of cells; hollow fibers and multilobal fibers may be especially important for their use in situations where absorbancy is needed. In addition, applications from sub-denier size fibers to sizes such as ribbons and tapes can be envisaged for those skilled in the art.

The fibers of the present invention are useful in the formation of a variety of devices. Some contemplated forms include fibers and/or yarns braided or twisted from one or more types of fibers, which are then woven, braided and/or knitted into fabrics, tubular or otherwise, fibrillar products, which are knitted, woven or felted, such as velours. The fibers of this invention are preferably used in the fabrication of implantable medical devices such as vascular implants, nerve channels; burn and wound covers; facial substitutes; orthopedic substitutes for bone or bone repair; breast prostheses; tendon and ligament replacements; hernia patches; and the like, or used as sutures and fasteners. Other devices not necessary for implantation purposes can also be envisaged, e.g., cell culture substrates, absorbants or swabs, medicated dressings, gauze, fabric, sheet, felt or sponge for hemostasis, dental packs and the like. A good description of the formation of bioresorbable materials in part, or in total as matted surgical dressings may be found in U.S. Pat. No. 3,937,223 to Roth.

Particularly useful are woven or knitted fabrics formed into tubes of varying shapes, lengths and diameters, to be implanted for short or long terms. Of these tubular protheses may be mentioned vascular and nerve guidance channels and the like. The particular configuration of such tubes may vary according to the size and shape of the organ to be repaired, and whether the intended repair is to take place in human surgery or in surgery involving other animal species.

The copolymers of the invention are particularly suited for use in the formation of vascular repair grafts. With particular regard to these vascular grafts or aortic patches, one skilled in the art should appreciate that in living tissue, a limited amount of macrophages infiltrate an area of tissue repair to aid in the removal of bioresorbable materials, and to aid in the formation of organized tissue such as capillary blood vessels. The copolymers of the present invention can induce this biological phenomenon.

In the preferred embodiments of the invention, especially for, vascular graft applications, the device is pretreated to provide a more compliant prostheses. Any conventional method can be used. One of the preferred pre-treatment methods is crimping. Illustrative of useful crimping methods is the method described in U.S. Pat. No. 3,337,673. In this method, the spacing and height can be controlled. The crimping of commercially-available Dacron vascular grafts (including both woven and knitted) was about one millimeter up and millimeter down from the mean diameter of the grafts. Crimping as such can be achieved by this method for the bioresorbable grafts.

In the preferred embodiments, the vascular graft is coated with a bioresorbable coating to improve graft patency. Preferably the desired coating is an amorphous polycarbonate, which has some solubility in a solvent which is is a non-solvent for the polymer forming the graft body. In general, the coating is applied to the graft by dissolving the coating polymer in a solvent which is a non-solvent for the graft polymer, and then dipping the graft body into the solution. Illustrative of useful solvents is dimethyl sulfoxide (DMSO), which will dissolve the amorphous polycarbonates which form the coating but not the extruded and more crystalline polymers which form the graft body. The coating solution containing up to about 10% solid can be made with DMSO. For example, a completely clean bioresorbable graft when dipped into a 4.5% solution (six dips, with inversion between each dip) yielded a roughly 25% weight gain. The grafts become slightly stiffer, but the fiber forming the graft body can still be separated down to the monofilaments.

The copolymers of the invention are also suited for use in ligament and tendon replacements. One skilled in the art should appreciate that again, organized tissue formation is encouraged by the use of the copolymers of this invention, and this will aid in the regeneration of certain elements of ligaments and tendons.

Similarly, the fibers of the invention are also contemplated to be particularly useful in dental and bone repair as fibers and fabric used in composite structures, and as fabric and fibers used by themselves with or without such materials as calcium hydroxyapatite, Bioglass, calcium triphosphate, drugs, and other components, however incorporated.

Similarly, fibers of the present invention may also be woven, felted, knitted, braided or the like into nerve guidance channels of many sizes and configurations. U.S. Pat. No. 3,833,002 to Palma discloses various sizes and shapes fabric may be formed into. Lengths of the tubes, internal diameters, and tubular wall thicknesses and wall porosity may vary according to intended use. The length of the tube would ordinarily be commensurate with the size of the nerve gap to be repaired, also allowing extra tubing in which to insert nerve stumps. The present inventors have found that particularly useful internal diameters commonly range from about 0.13 mm to 30.0 mm. Tapered tubular prostheses are also within the comtemplation of the invention.

Hollow fibers, with or without wall porosity, can be used for nerve channel applications and may be formed from the copolymers of the invention by an conventional techniques such as melt extrusion, solution extrusion, gel extrusion, other possible combinations of the above processes, and the like. However, it is particularly useful to employ an extrusion process wherein the hollow fiber or tube dimensions may be carefully controlled by the extruding die dimensions, differential gas pressure between inner and outer surfaces of the tube, melt draw down and subsequent orientation process. Die dimensions are easily selected by consideration of the inner and outer diameters of the nerve channel, die swell, extrusion rates, orientation in the melt and rubbery state. For nerve channels having the characteristics of the desirable dimensions and evenness, the usual procedure is to pressurize the tube with an inert gas to prevent collapsing the differential gas pressure is preferably maintained at about 0 to about 0.02 atm, most preferably 0 to about 0.004 atm. The melt draw down may be controlled by the ratio of average exit velocity out of the die and the take up velocity. The exit velocity for a given die and polymer viscosity is controlled by the extrusion pressure. Orientation is preferably effected by the ratio of speeds of two sets of rollers. Often a draw pin or heated surface is present between the rollers to stabilize the orientation process.

In particular, hollow fibers or tubings of this invention may be used for devices where bio- and/or blood compatibility is most desired, e.g., tubings for transfer of blood or other bodily fluids from one place to another. Similarly, hollow fibers are devices already in tubular form can also be used as vascular grafts, fallopian tube ducts and spare duct replacements, and the like. The range of internal diameter can vary widely depending on the vessel to be replaced; particularly useful range are commonly found to be 0.13 mm to 30 mm. For these applications, hollow fibers or tubes with or without wall porosity are contemplated.

Depending on the application, fibers that differ in modulus, although having the same fiber composition, can be obtained by cold draws of similar processes known to those skilled in the art. For those skilled in the art it should be appreciated that softened fibers are preferred in certain end applications such as wound dressing, swabs, wound or burn covers, as part of vascular protheses, and the like. Fiber of different or the same polymeric compositions and physical and mechanical properties but differing in denier can be obtained and used or fabricated into fabric that is woven, knitted, velveted, veloured, meshed or braided. Stable fibers can be obtained and processed to fabric such as felt, mat and the like. For example, the felted material may be used as, or be part of, skin or wound covers, reinforcements for suturing in surgery, and as aids for hemostasis. Velveted material is particularly suited for use in small caliber blood vessel replacements. Matted fabric may be used, for example, as swabs. Additionally, it should be appreciated that all these forms of fabric and fiber and yarn can be used as slow release drug carriers, not only limited to transdermal, but also used in implantable devices for long or short term procedures.

Thus, for those skilled in the art, it can be appreciated that aside from the polymeric composition and molecular weight and distribution of the copolymers of the invention, processing particular such as those described above can be profitably utilized or adjusted to achieve varying outcomes in biodegradation or bioresorption rates, hardness, toughness, softness, compliancy, adaptability, amenability to custom fabrication during manufacturing and also in the field during the application of the device. This includes combining fibers of the invention with other bioresorbable fibers, fabrics, or devices. For example, any combination with Vicryl, Maxon, Dexon, PDS (polydioxanone), and other polycarbonate-based fibers and like, is within the contemplation of the present invention.

However, the present inventors do not wish the applications of the fibers of this invention to be limited to totally biodegradable or bioresorbable devices. Fibers or yarns formed from the polycarbonates of the invention with or without other more biodurable components in the fiber or as part of a device, and/or combinations with other physical objects, are within the contemplation of the invention. These include, for example, but are not limited to, fabric and/or coated fabric in a permanent prosthesis or device, implanted into living organisms or otherwise, or fabric and yarn composed of a mix of fibers of the more biodurable, or biodurable fibers with the polycarbonate fibers, and the like.

The following are more specific examples of certain embodiments of the invention, but are not be construed as limitative thereof.

EXAMPLES

EXAMPLE 1

Synthesis of 5,5-Dimethyl-1,3-dioxan-2-one (DMTMC, Dimethyltrimethylene carbonate).

A three liter three-necked round bottom flask was fitted with mechanical stirrer, 12 inch Vigreux column with distilling head and a thermometer. In the flask were placed 838 g (8.05 moles) 2,2-dimethyl-1,3-propanediol and 1098 mL (9.07 moles) diethyl carbonate. The mixture was immersed in an oil bath, heating initiated, and the stirrer started. By the time the temperature reached about 90° C., the diol had melted and dissolved in the carbonate. Powdered, dry sodium methoxide (21.6 g, 0.4 moles) was added through the neck used for the thermometer. The bath temperature was raised to 160 ° C.; ethanol began to distill out.

Over a period of about three hours, approximately 600 g (80% of theoretical) of distillate was collected; this is mainly ethanol with some diethyl carbonate. The reaction mixture gradually became very thick. Dry xylene (200 mL) was added through the top of the distillation column and the bath temperature was raised to 170°–180 ° C. Additional distillate was collected and the pot temperature gradually climbed to about 150 ° C.; when the distillation rate had slowed to only a few drops a minute, vacuum was cautiously applied to the system and gradually increased as the xylene and excess diethyl carbonate distilled out.

When the vacuum reached about 2-5 mm Hg, the product carbonate began to distill at about 125°–135 ° C. At this point, the vacuum was released with dry nitrogen and the oil bath lowered. The Vigreux column and distilling head were removed and replaced with a short path distillation head. Additional powdered sodium methoxide (5.4 g, 0.1 moles) was added quickly through the thermometer port.

Vacuum was applied to the system and adjusted to about 3-5 mm Hg. Heating was resumed and the product began to distill out. The bath temperature was raised to 210°–220° C. gradually in order to maintain the depolymerization rate of the oligomers to generate the product monomer. Care had to be taken not to rush the distillation, so that depolymerization of the dimer and oligomers could occur; otherwise, the dimer would have begun to distill over. Eventually, the pot residue became a gummy lump coated with powder and distillation ceased. Total yield of distillate was 852 g (81% of theory).

The product was a slightly sticky solid due to contamination with small amounts of impurities, such as xylene, diethyl carbonate, the starting diol and the cyclic dimer. It was recrystallized as follows. The total crude DMTMC (852 g) was dissolved in 430 mL tetrahydrofuran and 4.3 liters of anhydrous diethyl ether was added cautiously. The liquors were allowed to stand at room temperature for about one-half hour, then placed in a refrigerator at 4° C. overnight. The crystals were collected by filtration, washed with cold ether (1.2 liters), with hexane (1.2 liters), and then by pulling air through the filter cake for about one hour. Final drying was in a vacuum oven at 35°–40° C. (0.1 mm Hg). Total recovery of purified DMTMC was 730 g (70% overall yield).

EXAMPLE 2

Copolymerization in sealed tube of DMTMC and Trimethylene Carbonate (TMC), 97.5:2.5

A mixture of freshly purified and dried DMTMC (14.64 g, 112.5 mmol) trimethylene carbonate (TMC, 378 mg, 3.7 mmol), and 2,2-dimethylpropanediol (12 mg, 0.116 mmol) was combined in a polymerization tube, evacuated, and the tube filled with argon. Stannous octoate (65 mL of $3 \times 10^{-2}$M solution in toluene) was added and the tube evacuated for several minutes. The tube was sealed with a torch, the contents melted and thoroughly mixed, then immersed in an oil bath at 160° C. overnight. After chilling in liquid nitrogen, the tube was broken, the contents dissolved in dioxane (250 mL), and precipitated into 1 L of ice water. The polymer was washed with water ($2 \times 500$ mL) and dried in vacuo overnight at 50° C. Yield: 13.1 g (87%); reduced viscosity 0.68 dL/g (0.1% in dioxane).

EXAMPLE 3

Copolymerization in resin flask of DMTMC and TMC, 97.5:2.5

An oven-dried, silanized glass 150 mL resin flask was equipped with mechanical stirrer with a teflon paddle, argon inlet, a serum cap on one port, and a glass stopper on the remaining port. To the flask were added freshly dried and purified DMTMC (29.25, 225 mmol), TMC (0.75 g, 7.4 mmol), and dimethypropanediol (12 mg, 0.12 mmol). The flask was evacuated and filled with argon several times, then immersed in an oil bath at 120° C. to melt the monomers. The temperature was raised to 145° C. in 10 minutes, then 125 mL of a $3 \times 10^{-2}$M solution of stannous octoate in toluene was added. The temperature was raised to 160° C. in another 10 minutes. Within another 10 minutes the material had become very thick and after one hour the reaction was stopped, the polymer was dissolved in chloroform and precipitated into 2-propanol. Yield: 24.4 g, (81%); reduced viscosity 0.80 dL/g (0.1% in dioxane).

EXAMPLE 4

Poly(DMTMC co TMC), 97,5:2.5

A polymerization was carried out as in the preceding example, with the following changes. The resin kettle was of 1 L capacity: 292.5 g DMTMC, 7.5 g TMC and 105 mg dimethylpropanediol were used. Initial heating was at 140° C. and the catalyst was 1605 mL of 1.0M stannous octoate in toluene. After 4 hours a total of 277 g of polymer was isolated from the flask; gel permeation chromatography (GPC) using THF showed a weight average molecular weight of 89,000 and a dispersity of 2.4 for the polymer peak, plus small amounts of oligomers. For spinning into fibers, the polymer was dissolved in dioxane and precipitated into water.

EXAMPLE 5

Copolymerization of DMTMC and Caprolactone, 98.2:1.8

A mixture of DMTMC (26.34 g, 202 mmol), freshly distilled caprolactone (.475 mL, .489 g (4.3 mmol), 2,2-dimethyl-1,3-propanediol (0.2 mmol) and stannous octoate (150 mL of 0.1M solution in toluene) was divided between three polymerization tubes. The tubes were sealed under vacuum and heated at 160° C. overnight. The resulting polymers were combined, dissolved in tetrahydrofuran and precipitated into water. Yield: 38.8 g (87%). Weight average molecular weight=89,000 by GPC (THF).

EXAMPLE 6

Poly(DMTMC co Caprolactone).

In an oven-dried, silanized 1 L resin flask were combined DMTMC (313.7 g, 2.41 mol), distilled caprolactone (5.62 g, 49 mmol) and 2,2-dimethyl-1,3-propanediol (63 mg, 0.60 mmol). After purging with argon the flask was heated to 160° C. in an oil bath; when the mixture had become homogenous, stannous octoate (155 mL of a 1.0M solution in toluene) was added. The mixture gradually became very thick; stirring was discontinued after 2.5 h and the reaction was stopped after an additional 3.5 h. The polymer was combined with those from two smaller runs, dissolved in tetrahydrofuran and precipitated into water. Yield: 650 g (92%). Weight average molecular weight - 89,300 by GPC (THF).

EXAMPLE 7

A series of copolymers of DMTMC with small amounts (2 to 5%) of TMC were evaluated. These were spun into approximately 70 denier filament. These polycarbonate copolymers could be melt spun easily in the temperature range 150° to 190° C. with good melt stability as indicated at a constant melt viscosity. Drawn samples, e.g., 4A and 4B (Table III), showed satisfactory fiber tensile strength properties for fabric and hollow fiber or tubular applications as nerve channels.

EXAMPLE 8

A higher molecular weight polycarbonate resin with reduced viscosity 1.1 of DMTMC and TMC (97.5:2.5) was extruded similarly as Example 6, (Table I), but with a melt temperature of 195° C. The 0.030 die used had an exit melt velocity of 0.3 ft/min. and taken up at about 30 ft/min. The fibers continued on to a set of draw godets and are subjected to increase in draw ratio. The test results, 15A to 15E, show good fiber properties for many fabric and hollow tube applications.

EXAMPLE 9

A copolymer of DMTMC and caprolactone of 98.2:1.8 weight ratio (Sample 29, Table II) was spun as in Example 7. Fibers from a number of draw ratios showed good tensile and hollow fiber or tube properties (see Example 29 A-D in Table III).

EXAMPLE 10

A sample of a 300 g batch of a copolymer of DMTMC with TMC (97.5 to 2.5 weight %) was prepared to provide information on conditions for spinning multifilament yarn. The material was melt spun as in Example 7 using a melt temperature of 180° C. The fibers were then drawn to yield tensile properties listed in Table III as Sample 22. Satisfactory properties for fabric and hollow fiber or tubing applications are indicated.

EXAMPLE 11

Polycarbonate polymer recovered from Example 10, dissolved and reprecipitated was melt spun at 180° C. with a lower melt draw down and oriented to give satisfactory fiber properties listed as Sample 22A in Table III.

TABLE I

RANDOM COPOLYMERS OF DMTMC (D) AND TMC (T)

| Sample Number | D:T Weight Ratio | Method of Synthesis | Quantity Isolated | Yield (%) | Reduced Viscosity |
|---|---|---|---|---|---|
| 1 | 95:5 | Example 2 | 11.3 g | 79 | 0.76 |
| 2 | 95:5 | Example 2 | 9.3 g | 62 | 0.77 |
| 3 | 97.5:2.5 | Example 2 | 11.9 g | 83 | 0.66 |
| 4 | 97.5:2.5 | Example 2 | 24.0 g | 82 | 0.53 |
| 5 | 97.5:2.5 | Example 2 | 24.3 g | 82 | 0.57 |
| 6 | 97.5:2.5 | Example 2 | 24.0 g | 80 | 0.71 |
| 7 | 97.5:2.5 | Example 2 | 37.5 g | 82 | 4.9 |
| 8 | 97.5:2.5 | Example 2 | 48.5 g | 83 | 5.6 |
| 9 | 97.5:2.5 | Example 2 | 13.1 g | 87 | 0.68 |
| 10 | 97.5:2.5 | Example 3 | 24.4 g | 81 | 0.80 |
| 11 | 97.5:2.5 | Example 2 | 26.6 g | 89 | 0.83 |
| 12 | 25:75 | Example 2 | 7.8 g | 89 | 0.86 |
| 13 | 97.5:2.5 | Example 3 | 25.0 g | 83 | 0.38 |
| 14 | 97.5:2.5 | Example 2 | 10.4 g | 87 | 1.46 |
| 15 | 97.5:2.5 | Example 2 | 10.4 g | 87 | 1.10 |
| 16 | 97.5:2.5 | Example 3 | 5.1 g | 85 | 0.91 |
| 17 | 97.5:2.5 | Example 2 | 5.3 g | 88 | 1.30 |
| 18 | 97.5:2.5 | Example 4 | 90.0 g | 90 | 0.43 |
| 19 | 97.5:2.5 | Example 2 | 8.3 g | 83 | |
| 20 | 97.5:2.5 | Example 4 | 90.0 g | 90 | |
| 21 | 97.5:2.5 | Example 4· | 282 g | 94 | |
| 22 | 97.5:2.5 | Example 4 | 277 g | 92 | |
| 23 | 97.5:2.5 | Example 4 | 291 g | 97 | |
| 24 | 96.8:3.2 | Example 2 | 9.8 g | 94 | |

| Sample Number | GPC Main Peak Wt Av | GPC Main Peak MW Disp. | GPC Overall Wt Av | GPC Overall MW Disp. |
|---|---|---|---|---|
| 1 | | | | |
| 2 | | | | |
| 3 | | | | |
| 4 | | | | |
| 5 | | | | |
| 6 | | | | |
| 7 | | | | |
| 8 | | | | |
| 9 | | | | |
| 10 | | | | |
| 11 | | | | |
| 12 | | | | |
| 13 | | | | |
| 14 | | | 150,000 | 18.80 |
| 15 | | | 115,000 | 7.93 |
| 16 | 64,300 | 3.10 | 62,000 | 10.20 |
| 17 | | | | |
| 18 | 35,100 | 4.00 | | |
| 19 | 62,500 | 2.88 | 80,500 | 13.40 |
| 20 | 85,600 | 4.36 | 86,700 | 29.30 |
| 21 | 142,000 | 3.57 | 127,000 | 37.60 |
| 22 | 88,700 | 2.38 | 82,500 | 17.80 |
| 23 | 113,000 | 3.60 | 108,000 | 18.40 |
| 24 | 257,000 | 3.48 | 257,000 | 28.20 |

TABLE II

RANDOM COPOLYMERS OF DMTMC (D)/ CAPROLACTONE (CL) AND DMTMC (D)/d,1-LACTIDE

| Sample Number | D:CL Ratio | Method of Synthesis | Quantity Isolated | Yield (%) |
|---|---|---|---|---|
| 27 | 98.2:1.8 | Example 6 | 54.3 g | 84 |
| 28 | 98.2:1.8 | Example 6 | 62.0 g | 95 |
| 29 | 98.2:1.8 | Example 5 | 38.8 g | 87 |
| 30 | 98.2:1.8 | Example 6 | 650 g | 92 |
| 31 | 95.6:4.4 | Example 5 | 9.4 g | 95 |
| 32 | 77.4:22.6 | Example 5 | 9.6 g | 96 |
| 33 | 53.3:46.7 | Example 5 | 8.8 g | 93 |
| 34 | 91.1:8.9 | Example 5 | 8.3 g | 88 |
| 35 | 87.8:12.2* | Example 5 | 8.6 g | 86 |

*87.8 = D:12.2 = d, 1-Lactide

| Sample Number | GPC Main Peak Wt- Av- | GPC Main Peak MW Disp. | GPC Overall Wt- Av- | GPC Overall MW Disp. |
|---|---|---|---|---|

TABLE II-continued
RANDOM COPOLYMERS OF DMTMC (D)/ CAPROLACTONE (CL) AND DMTMC (D)/d,1-LACTIDE

| 27 | 46,500  | 2.03 |         |       |
|----|---------|------|---------|-------|
| 28 | 124,000 | 2.50 | 150,000 | 16.30 |
| 29 | 99,500  | 1.34 | 89,000  | 29.53 |
| 30 | 91,500  | 2.42 | 89,300  | 4.79  |
| 31 | 132,000 | 2.36 | 156,000 | 11.50 |
| 32 | 104,100 | 1.63 | 170,200 | 2.85  |
| 33 | 14,800  | 2.06 | 14,900  | 2.07  |
| 34 | 10,100  | 2.39 | 88,900  | 29.50 |
| 35 | 88,900  | 2.54 | 87,000  | 6.65  |

General Procedures for Biopolymer Spinning

Biopolymers such as DMTMC/TMC and DMTMC/CL were spun using the following equipment and procedures:

Dry polymer was charged into a hopper of a Braebender ¾ inch extruder equipped with two adjustable electrically heated zones and a heated block assembly consisting of an electrically heated metal block and No. 2 Zenith gear pump. The spinnerette consisted of a stainless steel (316) die, containing 8 holes, 0.21" diameter and a 200 mesh screen pack.

Feed rate, extrusion temperatures and pressures are presented in Examples 12 and 13.

The filaments were air quenched and taken up on a constant speed godet set at 1448 ft/min. The second godet was set at 2854 ft/min. which resulted in a draw ratio of 2:1. Yarn haul off was made using a Leesona winder.

EXAMPLE 12

Run Parameters
Material 97.5% DMTMC - 2.5% TMC, Samples 21-23 (Table I).
Extruder: ¾ Braebenders
Heat:
Zone 1 (feed) 200° C.
Zone 2 (metering) 212° C.
Zone 3 (die and block) 215° C.
Screen Pack 200 mesh
Die 8 hole .021" diameter
Screw RPM: 186
Pump RPM in percent: ~22
Pressure barrel: 1200 psi
Pressure die: 600 psi
Take up:
Roll 1/temperature: 1448 ft/min. at R.T.
Roll 2/temperature: 2854 ft/min. at R.T.
Final thruput: 0.4 gms/hole/min.
Final draw ratio: ~2:1
Denier: 5 DPF towed to 200/40

EXAMPLE 13

Run Parameters
Material 98.2% DMTMC - 1.8% CL, Sample 30 (Table II)
Extruder: ¾" Brawbender
Heat:
Zone 1 (feed) 190° C.
Zone 2 (metering) 200° C.
Zone 3 (die and block) 210° C.
Screen Pack: 200 mesh
Die 8 hole: .021" diameter
Screw RPM: ~22
Pressure barrel: 1200 psi
Pressure die 600 psi
Take up:
Roll 1/temperature: 1448 ft/min. at R.T.
Roll 2/temperature: 2854 ft/min. at R.T.
Final thruput: 0.4 gms/hole/min.
Final draw ratio: 2:1
Denier: 5 DPF towed to 200/40

TABLE III

| | | Fiber Mechanical Properties | | |
|---|---|---|---|---|
| Sample | Denier | Tensile Modulus (g/d) | Tensile Strength (g/d) | Ultimate Elongation (%) |
| 4A  | 10  | 90 | 5.5 | 16 |
| 4B  | 13  | 70 | 3.4 | 24 |
| 10  | 198 | 22 | 0.3 | 7  |
| 15A | 33  | 37 | 1.4 | 24 |
| 15B | 19  | 41 | 1.5 | 29 |
| 15C | 17  | 51 | 2.5 | 26 |
| 15D | 17  | 57 | 2.7 | 23 |
| 15E | 4   | 82 | 4.0 | 17 |
| 29A | 13  | 45 | 3.4 | 50 |
| 29B | 13  | 43 | 3.7 | 53 |
| 29C | 13  | 50 | 3.7 | 49 |
| 29D | 11  | 88 | 4.4 | 20 |
| 22  | 12  | 62 | 4.5 | 27 |
| 22A | 48  | 45 | 4.8 | 30 |
| 24  | 29  | 43 | 2.9 | 43 |

EXAMPLE 14

Completely Bioresorbable Graft:

1. Compositions: Fiber A=97.5% DMTMC/2.5% TMC and fiber B=98.2% DMTMC/1.8% ε-caprolactone.

2. Fibers: as obtained from Examples 12 and 13.

3. Weaving: The 200 denier fiber was twisted 7.125 turn/inch when repackaged, to be used for the filling (horizontal) and wrap (vertical) construction to keep the monofilaments together. The fabrics were a plain weave tube with both warp and fill directions having the same fiber, at a construction of 120 total body ends by 120 picks per inch (that is a perfect square, tight weave). The total circumferences were 18.8 and 25.2 mm for each of the fibers used, which correspond to 6 and 8 mm diameter respectively. Some obviously defective areas were found from time to time due to slight changes of tension on the fill bobbin, and also due to the knots in the towed fiber.

4. The flat fabric was heat-set between 60° to 90° C. to round (cross section) with a glass mandrel and cleaned with 0.05% Triton X-100 detergent in 50% ethanol-water, then rinsed 6 times with water, and finally rinsed with absolute ethanol. The operation was performed inside a class 100 laminar flow hood upto and including packaging of the device in sterilization pouches.

5. Standard cold cycle ethylene oxide was used to sterilize these completely bioresorbable vascular grafts.

6. The water permeation rates at 120 mm Hg pressure after heat-set of such prostheses were below 500 cc/cm²/minute. They were implanted bilaterally in sheep as carotid replacements without preclotting. No complications resulted.

EXAMPLE 15

Tendon and Ligament Replacement Devices
A. Uniaxial towed fiber device

A bundle of well-aligned fibers, roughly with cross-sectional dimensions of 5–6 mm by 0.4–0.5 mm and with a length of 45 cm are fastened onto two surgical needles. The devices is cleaned with 0.05% Triton X-100 in 50% ethanol-water, then rinsed six times with water, and finally rinsed with absolute alcohol. The operation is performed inside a class 100 laminar flow hood from the cleaning of the device up to and including packaging of the device in sterilization bags. Standard cold cycle ethylene oxide is used to sterilize these devices.

The device of this size is useful for tendon or ligament replacements in small animals, e.g., the Achilles tendon in rabbits.

B. Braided and crocheted fabric devices

Six yarns of twisted fibers are braided together to form a strand of fabric, 45 mm in length, and with cross-sectional dimensions of 1 mm by 6 mm. Similarly, yarns are crocheted into devices of various cross-sectional diameters and lengths, depending on the end application. These fabrics are cleaned as discussed above, and are to be used as replacement devices for ligaments and tendons in small animals.

EXAMPLE 16

Copolymerization of DMTMC and TMC in Xylene Solution.

In an oven-dried 100 mL resin flask DMTMC (7.81 g, 60 mmol), TMC (6.13 g, 60 mmol) and dimethylpropanediol (3 mg) were combined. The flask was evacuated to 0.1 mm Hg for ten minutes, then filled with dry argon. Xylene (15 mL), dried by distilling from sodium metal, was added to the flask by syringe, then the flask was immersed in an oil bath at 150° C. After stirring for five minutes, tin octoate (25 mL of a 1.0M solution in toluene) was added. The solution became very viscous over a two hour period; a sample (ca. 200 mg) was taken and diluted with 5µL tetrahydrofuran. Analysis of GPC showed a weight average molecular weight of 142,000. The solution was precipitated into methanol, the polymer washed with methanol and dried. NMR analysis of the precipitated sample showed a TMC content of 51% and DMTMC content of 49%. From the carbonyl carbon region of the 100 MHz carbon spectrum, it was determined that the carbonate groups of the polymer consisted of 27% DMTMC-DMTMC linkages, 28% TMC-TMC linkages and 45% DMTMC-TMC linkages.

EXAMPLE 17

Completely Bioresorbable Crimped and Coated Graft:

1. Totally bioresorbable 6 mm vascular grafts were woven from Fiber A & B as described in Example 14, sections 1 to 3. Crimping according to the general method of Jekel (U.S. Pat. No. 3,337,673) was used. Thus, the spacer was provided by a cotton string helically wound on the fabric graft body with a glass mandrel inserted into the lumen. Crimp-shape was formed by slowly forcing the two ends of the graft towards the middle. The crimping can be set to as small as 0.5 millimeter up and 0.1 to 0.2 mm down so that the internal surface appears to be almost smooth but still resist kinking. After heat-setting, cleaning was done according to section 4 of example 14.

A solution containing 2 to 3% coating polymer, e.g., 91% TMC - 9% 1-lactide, was made with solvent DMSO. The clean bioresorbable graft was dipped into said solution with six dips, inverting between each dip, to yield a 10% weight gain. The dipping was performed inside a Class 100 laminer flow hood.

2. Standard cold cycle ethylene oxide was used to sterilize these completely bioresorbable coated and crimped vascular grafts.

3. The water permeation rates at 120 mm Hg pressure of such prostheses were about 400 cc/cm$^2$minute. They were implanted bilaterally in sheep as carotid replacements without preclotting. No complication resulted. The patency rate at 12-week stands at 100% (6 out of 6 grafts) for these 6 mm, total bioresorbable, crimped and coated vascular grafts.

What is claimed is:

1. A copolymer of fiber forming molecular weight comprising as a major component one or more recurring monomeric units selected from the group consisting of recurring monomeric units of the following General Structure I and Structure II:

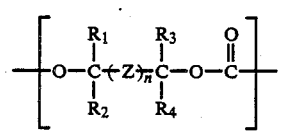

Structure I

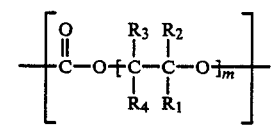

Structure II wherein:

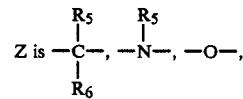

or a combination thereof, where Z is selected such that there are no adjacent heteroatoms;

n and m are the same or different at each occurrence and are integers from about 1 to 8; and $R_1$, $R_2$, $R_3$, and $R_4$ are the same or different at each occurrence and are hydrogen, aryloxyalkyl, alkoxyaryl, aryloxyaryl, arylalkyl, alkylarylalkyl, arylalkylaryl, alkylaryl, arylcarbonylalkyl, aryloxyalkyl, alkyl, aryl, alkylcarbonylalkyl, cycloalkyl, arylcarbonylarly, alkylcarbonylaryl, alkoxyalkyl, or phenyl or alkyl substituted with one or more biologically compatible substituents;

$R_5$ and $R_6$ are the same or different and are $R_1$, $R_2$, $R_3$ $R_4$, dialkylamino, diarylamino, alkylarylamino, alkoxy, aryloxy, alkanoyl, or arylcarbonyl; or any two of $R_1$ to $R_6$ together can form an alkylene chain completing a 3, 4, 5, 6, 7, 8 or 9 membered alicyclic, spiro, bicyclic and/or tricyclic ring system, which system may optionally include one or more non-adjacent carbonyl, oxa, alkylaza or arylaza groups; with the proviso that at least one of $R_1$ to $R_6$ is other than hydrogen; wherein the amount of said major component in said copolymer is at least about 77.4% by weight based on the total weight of recurring monomeric units in said copolymer.

2. The copolymer of claim 1 wherein $R_1$, $R_2$, $R_3$ and $R_4$ are the same or different and are selected from the group consisting of hydrogen, alkyl, cycloalkyl, alkoxyalkyl, aryloxyalkyl, aryloxyaryl, arylalkyl and aryl and arylalkyl groups substituted with one or more alkyl, alkoxy and alkoxyalkyl groups.

3. The copolymer of claim 2 wherein $R_1$, $R_2$, $R_3$, and $R_4$ are the same or different and are selected from the groups consisting of hydrogen, alkyl, cycloalkyl, alkoxyalkyl, phenylalkyl, and phenyl substituted with one or more alkyl or alkoxy groups.

4. The copolymer of claim 3 wherein said major component is a recurring unit wherein Z is selected from the group consisting of:

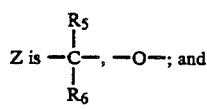

wherein n is 1, 2 or 3.

5. The copolymer of claim 4 wherein $R_1$ to $R_6$ are selected from the group consisting of aliphatic moieties up to about 10 carbon atoms and aryl moieties up to about 16 carbon atoms.

6. The copolymer of claim 5 wherein n the major component is of the Structural Formula I, n is 1 and Z is selected from the group consisting of:

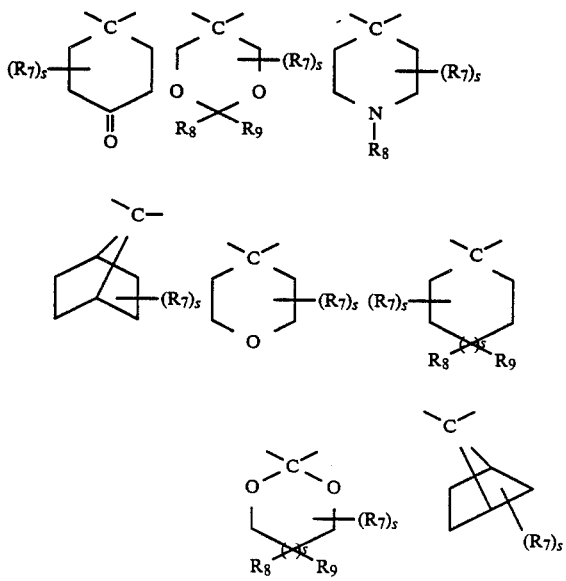

wherein:
$R_7$ is the same or different at each occurrence and is aryl, alkyl or an alkylene chain completing a 3 to 16 membered ring structure; $R_8$ and $R_9$ are the same or different and are $R_7$ or hydrogen;
s is the same or different at each occurrence and is 0 to about 3; wherein the open valencies are substituted with hydrogen atoms.

7. The copolymer of claim 5 wherein the major component comprises recurring moieties selected from the group consisting of:

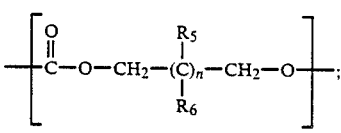

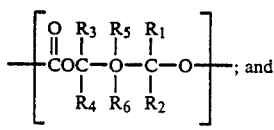

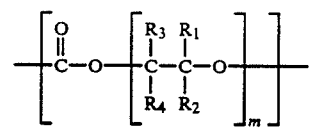

wherein:
$R_1$, $R_2$, $R_3$, and $R_4$, are the same or different at each occurrence and are hydrogen, alkyl, phenyl, phenylalkyl, alkoxyalkyl phenyl substituted with one or more alkyl or alkoxy groups;
$R_5$ and $R_6$ are the same or different and are $R_1$ to $R_4$, alkoxy, alkanoyl, dialkylamino, or $R_5$ and $R_6$ together may form an alkylene chain completing a 4, 5, 6, 7, 8, 9, or 10 membered spiro, bicyclic and/or tricyclic ring structure which structure may optionally include one or more non-adjacent divalent carbonyl, oxa, arylaza or alkylaza groups, with the proviso that at least one of $R_5$ or $R_6$ is other than hydrogen; and
n and m are the same or difference and are 1, 2 or 3.

8. The copolymer of claim 1 comprising as a major component recurring units of the formula:

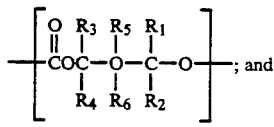

wherein:
$R_1$ to $R_4$ are the same or different and are alkyl, hydrogen, alkoxyalkyl, phenylalkyl, alkoxyphenyl, or alkylphenyl, wherein the aliphatic moieties include from about 1 to about 9 carbon atoms; and
$R_5$ and $R_6$ are the same or different at each occurrence and are selected from the group consisting of $R_1$ to $R_4$ substituents, aryloxy, and alkoxy, or $R_5$ and $R_6$ together form an aliphatic chain completing a 3 to 10 membered ring structure, with the proviso that at least one of $R_5$ or $R_6$ is other than hydrogen.

9. The random copolymer of claim 8 comprising as a major component, recurring monomeric units having the following Structure:

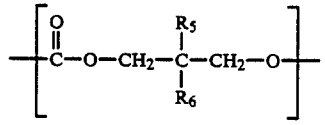

wherein:
$R_5$ and $R_6$ are the same or different and are hydrogen, phenyl, phenylalkyl, phenyl substituted with one or more alkyl, alkyl, or alkoxy groups; or $R_5$ and $R_6$ together may form a divalent alkylene chain forming a 3 to 10 membered spiro or bicyclic ring structure which may optionally include one or more non-adjacent divalent carbonyl or oxa groups, with the proviso that at least one of $R_5$ and $R_6$ is other than hydrogen.

10. The copolymer of claim 9 wherein $R_5$ and $R_6$ are the same or different and are phenyl, phenylalkyl, alkyl phenyl, alkyl, or a divalent chain forming a 4 to 7 membered ring structure.

11. The copolymer of claim 10 wherein $R_5$ and $R_6$ together form a divalent alkylene chain forming a 5 to 7 membered, spiro, bicyclic, or tricyclic ring structure.

12. The copolymer of claim 11 wherein said ring structure includes one or more non-adjacent divalent carbonyl, or oxa groups.

13. The copolymer of claim 10 wherein $R_5$ and $R_6$ are the same.

14. The copolymer of claim 10 wherein $R_5$ and $R_6$ are the same or different and are phenyl, alkylphenyl or phenylalkyl.

15. The copolymer of claim 14 wherein $R_5$ and $R_6$ are the same or different and are phenyl.

16. The copolymer of claim 15 wherein $R_5$ and $R_6$ are both phenyl.

17. The copolymer of claim 9 wherein said minor component is selected from the group consisting of orthocarbonates, orthoesters, delta lactones, trimethylene carbonate, dimethylene carbonate, and tetramethylene carbonate.

18. The copolymer of claim 17 wherein said minor component is trimethylene carbonate.

19. The copolymer of claim 18 wherein $R_5$ and $R_6$ of said major component are the same and are methyl.

20. A fiber comprising a copolymer having as a major component, a recurring carbonate monomeric unit having the structure:

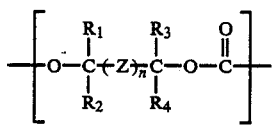

wherein

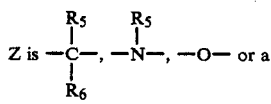

combination thereof; wherein n is any integer from about 1 to 8; and $R_1$, $R_2$, $R_3$, and $R_4$ are the same or different at each occurrence and are hydrogen, aryloxyalkyl, alkoxyaryl, aryloxyaryl, arylalkyl, alkylarylalkyl, arylalkylaryl, alkylaryl, arylcarbonylalkyl, aryloxyalkyl, alkyl, aryl, alkylcarbonylalkyl, cycloalkyl, arylcarbonylaryl, alkylcarbonylaryl, alkoxyalkyl, or phenyl or alkyl substituted with one or more biologically compatible substituents such as alkyl, aryl, alkoxy, aryloxy, dialkylamino, diarylamino, alkylarylamino substituents; or any two of $R_1$ to $R_4$ can form an alkylene chain completing a 3, 4, 5, 6, 7, 8 or 9 membered alicyclic fused, spiro, bicyclic or tricyclic ring system, which system may optionally include one or more non-adjacent carbonyl, oxa, alkylaza or arylaza groups;

$R_5$ and $R_6$ are the same or different and are $R_1$, $R_2$, $R_3$ $R_4$, dialkylamino, diarylamino, alkylarylamino, alkoxy, aryloxy, alkanoyl, or arylcarbonyl, provided that at least one of $R_5$ or $R_6$ is other than hydrogen; or any two of $R_5$ or $R_6$ together can form an alkylene chain completing a 3, 4, 5, 6, 7, 8 or 9 membered alicyclic, spiro, bicyclic or tricyclic ring system, which system may optionally include one or more non-adjacent carbonyl, oxa, alkylaza or arylaza groups.

21. An implantable bioresorbable medical device comprising at least one layer of a network of bioresorbable fibers selected from the group consisting of fibers of claim 20, said fibers interrelated to form said network.

22. An implantable bioresorbable medical device comprising a body having at least one portion which is fabricated totally or in part from the copolymer of claim 1, said portion is bioresorbable in the presence of living tissue.

23. A medical device according to claim 22 which further comprises a biodurable portion.

24. A copolymer according to claim 1 wherein the amount of said major component in said copolymer is from about 80 to about 99% by weight based on the total weight of recurring monomeric units in said copolymer.

25. A copolymer according to claim 24 wherein said amount is from about 90 to about 98% by weight.

26. A bioresorbable fiber forming copolymer comprising as a major component one or more recurring monomeric units of the formula:

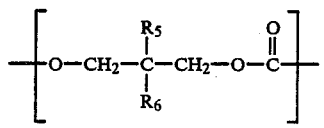

wherein:

$R_5$ and $R_6$ are the same or different and are hydrogen or alkyl having from 1 to about 7 carbon atoms;

wherein the amount of said major component in said copolymer is at least about 77.4% by weight based on the total weight of recurring monomeric units in the copolymer.

27. The copolymer of claim 26 wherein $R_5$ and $R_6$ are the same or different and are alkyl.

28. The copolymer of claim 27 wherein $R_5$ and $R_6$ are the same or different and are lower alkyl of from about 1 to 7 carbon atoms.

29. The copolymer of claim 28 wherein $R_5$ and $R_6$ are the same or different and are selected from the group consisting of methyl, ethyl, propyl, isopropyl, n-butyl, secondary butyl, tertiary butyl, pentyl, neopentyl, and hexyl.

30. The copolymer of claim 29 wherein $R_5$ and $R_6$ do not differ from each other by more than about 3 carbon atoms.

31. The copolymer of claim 29 wherein $R_5$ and $R_6$ do not differ from each other by more than about 2 carbon atoms.

32. The copolymer of claim 31 wherein $R_5$ and $R_6$ are alkyl of about 1 to 4 carbon atoms.

33. The copolymer of claim 32 wherein $R_5$ and $R_6$ are alkyl of about 1 to 2 carbon atoms.

34. The copolymer of claim 33 wherein $R_5$ and $R_6$ are the same and are methyl.

35. The copolymer of claim 26 wherein said second minor component is selected from the group consisting of substituted carbonates, non-substituted carbonates, lactones, dioxebanones, dioxanones, epoxides, epoxide/$CO_2$, anhydrides, orthoesters, and orthocarbonates.

36. The copolymer of claim 35 wherein said minor component is selected from the group consisting of ortho carbonates, orthoesters, delta lactones, trimethylene carbonates, dimethylene carbonate, and tetramethylene carbonates.

37. The copolymer of claim 36 wherein said minor component is trimethylene carbonate.

38. A copolymer according to claim 26 wherein the amount of said major component in said copolymer is from about 80 to about 99% by weight based on the total weight of recurring monomeric units in said copolymer.

39. A copolymer according to claim 38 wherein said amount is from about 90 to about 98% by weight.

40. The copolymer of claim 26 wherein $R_5$ and $R_6$ are alkyl.

41. The copolymer of claim 40 wherein $R_5$ and $R_6$ are the same.

42. The copolymer of claim 40 wherein $R_5$ and $R_6$ are alkyl of from 1 to about 4 carbon atoms.

43. The copolymer of claim 42 wherein $R_5$ and $R_6$ are alkyl of from 1 to about 2 carbon atoms.

* * * * *

UNITED STATES PATENT AND TRADEMARK OFFICE
CERTIFICATE OF CORRECTION

PATENT NO. : 4,891,263

DATED : January 2, 1990

INVENTOR(S) : A.M. Kotliar et al.

It is certified that error appears in the above-identified patent and that said Letters Patent is hereby corrected as shown below:

Col. 24, line 29, "difference" should read --different--

Col. 24, lines 3 to 7,

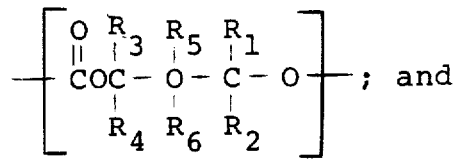
; and should read 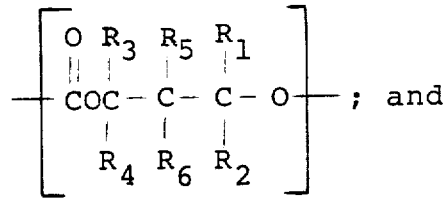 ; and

UNITED STATES PATENT AND TRADEMARK OFFICE
CERTIFICATE OF CORRECTION

PATENT NO. : 4,891,263
DATED : January 2, 1990
INVENTOR(S) : A.M. Kotliar et al.

It is certified that error appears in the above-identified patent and that said Letters Patent is hereby corrected as shown below:

Col. 24, lines 34 to 38,

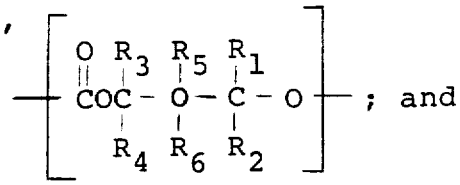
; and should read

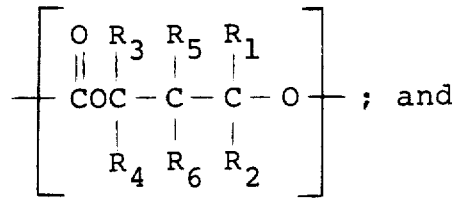
; and

Col. 27, line 2, "dioxebanones" should read --dioxpanones--

Signed and Sealed this

Twenty-ninth Day of January, 1991

*Attest:*

HARRY F. MANBECK, JR.

*Attesting Officer*     *Commissioner of Patents and Trademarks*